United States Patent [19]
Gall et al.

[11] Patent Number: 5,465,285
[45] Date of Patent: Nov. 7, 1995

[54] X-RAY EXAMINATION APPARATUS HAVING AN X-RAY FILM CASSETTE LOADING AND POSITIONING DEVICE

[75] Inventors: Arthur Gall, Langensendelbach; Heinz Meier, Nuernberg; Wilko Kuphal, Rueckersdorf; Georg Vogel, Bubenreuth, all of Germany

[73] Assignee: Siemens Aktiengesellschaft, Munich, Germany

[21] Appl. No.: 304,604

[22] Filed: Sep. 12, 1994

Related U.S. Application Data

[63] Continuation of Ser. No. 29,544, Mar. 11, 1993.

[30] Foreign Application Priority Data

Mar. 30, 1992 [DE] Germany ............... 42 10 421.1

[51] Int. Cl.⁶ ............................................. G03B 42/02
[52] U.S. Cl. ....................... 378/173; 378/174; 378/175
[58] Field of Search ................................. 378/173–175

[56] References Cited

U.S. PATENT DOCUMENTS 4,086,493  4/1978  Krumrey et al. ................. 378/173

FOREIGN PATENT DOCUMENTS 3034282  4/1982  Germany .
3344647  6/1985  Germany .

OTHER PUBLICATIONS

Siemens Brochure "SIREMAT Vollautomatischer Röntgen–Diagnostick–Arbeitsplatz mit Magazintechnik".

Primary Examiner—Craig E. Church
Attorney, Agent, or Firm—Hill, Steadman & Simpson

[57] ABSTRACT

An x-ray examination apparatus has an x-ray radiator mounted on a radiator carrier, with an x-ray film cassette loading and positioning device arranged relative to the radiator carrier so that an x-ray film cassette can be loaded into the device at a position remote from the x-ray radiator, and can be conveyed by the device, after loading, to an exposure position disposed beneath the x-ray radiator.

3 Claims, 2 Drawing Sheets

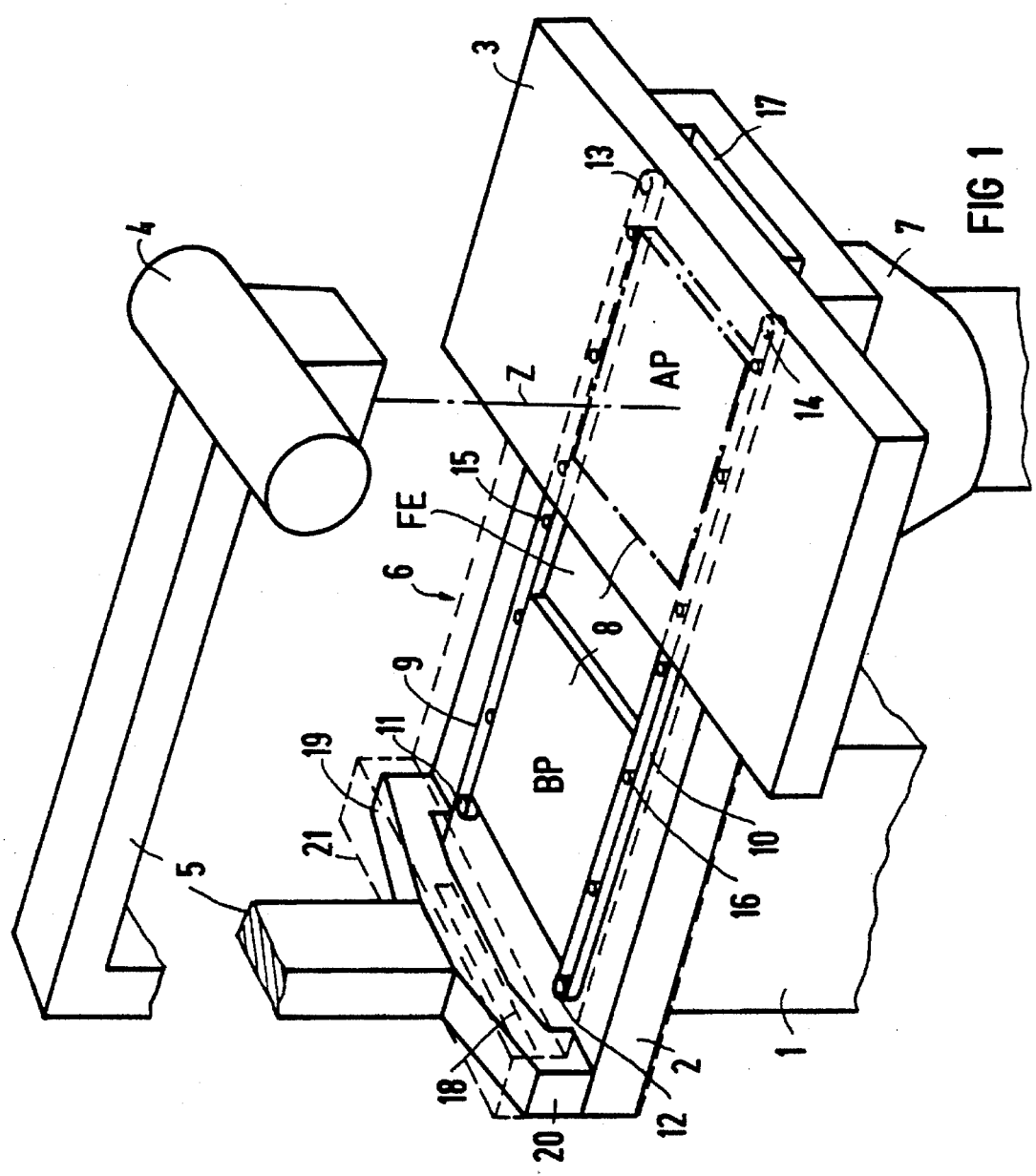

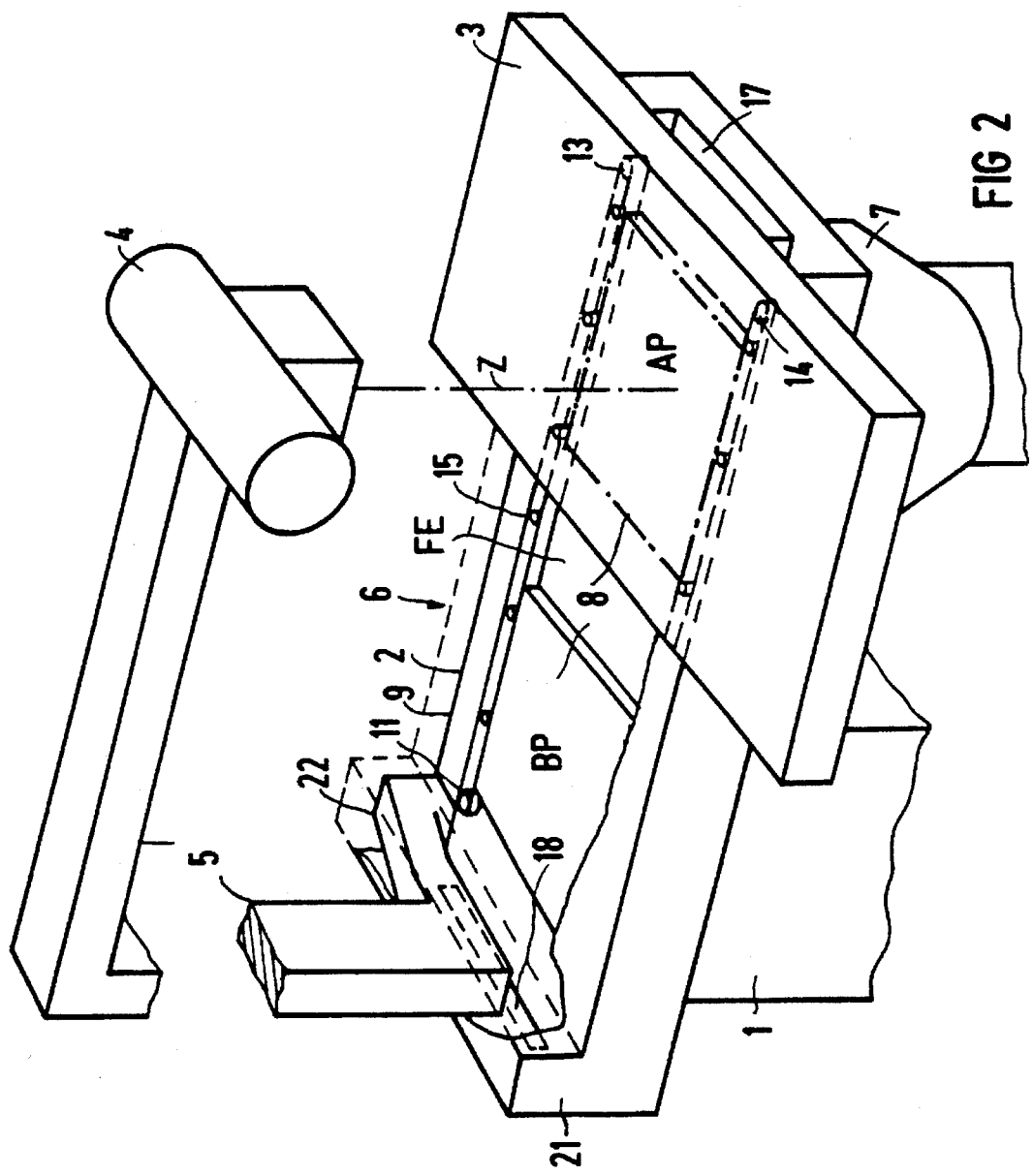

X-RAY EXAMINATION APPARATUS HAVING AN X-RAY FILM CASSETTE LOADING AND POSITIONING DEVICE

This is a continuation of application Ser. No. 08/029,544, filed Mar. 11, 1993.

BACKGROUND OF THE INVENTION

1. Field of the Invention

The present invention is directed to an x-ray examination apparatus for generating x-ray exposures using an x-ray film cassette, and in particular to such an apparatus having an x-ray radiator mounted on a radiator carrier, with an x-ray film cassette loading and positioning device for moving an x-ray film cassette from a stand-by position to an exposure position. Such x-ray film cassette loading and positioning device is also referred to in the art as spotfilm device.

2. Description of the Prior Art

AN x-ray apparatus is disclosed in German OS 33 44 647, for example, having an x-ray radiator mounted on a radiator carrier, with an x-ray film cassette loading and positioning device provided for conveying an x-ray film cassette from a loading opening, through which the x-ray film cassette is introduced into the device, to a readiness or stand-by position, and/or from the stand-by position to an exposure position beneath the x-ray radiator. It is a problem in systems of this type to construct the overall arrangement of the components so that the radiator carrier does not represent an obstacle for loading and positioning the x-ray film cassette. This can result in a structurally complicated and thus a costly structure for the x-ray examination apparatus.

Moreover, it is desirable, and known, to provide a loading device which permits an x-ray film cassette to be loaded from two sides, as described in German OS 30 34 282. In the aforementioned German OS 33 44 647, however, the structure selected to avoid the radiator carrier from presenting an obstacle to cassette loading has prevented two-sided loading from being available, because the radiator carrier would block a second loading opening (if it were provided), or would block the conveying path of an x-ray film cassette introduced through such a second loading opening.

SUMMARY OF THE INVENTION

It is an object of the present invention to provide an x-ray examination apparatus of the type having an x-ray radiator mounted on a radiator carrier wherein the radiator carrier does not constitute an obstacle in the selection of the cassette conveying direction in an associated x-ray film cassette loading and positioning device.

It is a further object of the present invention to provide such an apparatus wherein two-sided loading of the x-ray film cassette into the loading and positioning device is available.

The above object is achieved in accordance with the principles of the present invention in an x-ray examination apparatus having an x-ray radiator mounted on a radiator carrier, and having an x-ray loading and positioning device having a film plane. The radiator carrier is attached to the loading and positioning device in a region adjacent the film plane so that an x-ray film cassette can be loaded into, and conveyed through, the loading and positioning device from a side of the radiator carrier remote from the x-ray radiator, to an exposure position disposed beneath the x-ray radiator. In the apparatus disclosed herein, the region of the radiator carrier neighboring the film plane is constructed so that it does not represent an obstacle for the x-ray film cassette. This region of the radiator carrier may be the end of a section of the radiator carrier having a longitudinal axis which intersects the conveying path of the x-ray film cassette, this end being adjacent to the film plane.

The conveying direction within the loading and positioning device can therefore be selected in a manner which is most beneficial for a simple, economic and space-saving structure of the x-ray examination apparatus. Because the portion of the loading and positioning device to which the radiator carrier is attached does not have an impediment to loading the x-ray film cassette from that side of the device, the conditions for two-sided loading have been created, and thus a further loading opening can be provided at an opposite side of the device, i.e., at an opposite side of the exposure position, thereby permitting an x-ray film cassette to be loaded from either side of the exposure position.

In a further embodiment of the invention, the region of the radiator carrier which is adjacent the film plane can be forked so as to form two legs attached to the loading and positioning device, with the x-ray film cassette being introducible therebetween. The region of the radiator carrier in a further embodiment may have only a single leg attached to the loading and positioning device, with the x-ray film cassette being introducible through a loading opening beneath that leg.

DESCRIPTION OF THE DRAWINGS

FIG. 1 is a perspective view of an x-ray examination apparatus constructed in accordance with the principles of the present invention, in a first embodiment.

FIG. 2 is a perspective view of an x-ray examination apparatus constructed in accordance with the principles of the present invention, in a second embodiment.

DESCRIPTION OF THE PREFERRED EMBODIMENTS

An x-ray examination apparatus constructed in accordance with the principles of the present invention is shown in FIG. 1, and has a base 1 on which a carrier 2 is mounted at one end of the carrier 2, the carrier 2 forming a part of an x-ray film cassette loading and positioning device, generally referenced 6. A patient support table 3 is mounted at the opposite end of the carrier 2, the patient support table 3 having a longitudinal axis proceeding substantially transversely relative to the carrier 2. The examination apparatus also includes an x-ray radiator 4 which is attached to one end of an angled radiator carrier 5, so that, in the exemplary embodiment of FIG. 1, the x-ray radiator 4 is disposed above the patient support table 3. The radiator carrier 5 has an end remote from the x-ray radiator 4 which is connected to the carrier 2.

The examination apparatus also includes an x-ray image intensifier 7 disposed beneath the carrier 2 in registry with the x-ray radiator 4.

An x-ray film cassette 8 can be conveyed within the loading and positioning device 6 in a direction proceeding substantially perpendicularly to the longitudinal axis of the patient support table 3. The x-ray film cassette 8 can be conveyed from a readiness or stand-by position BP, disposed above the base 1 in the exemplary embodiment, into an exposure position AP situated beneath the patient support table 3 and in registry with the x-ray radiator 4.

The components for conveying the x-ray film cassette 8 within the loading and positioning device 6 include, as is known, two conveyor belts 9 and 10, which are respectively conducted around motor-driven drive rollers 11 and 12 and around respective deflection rollers 13 and 14. Respective sets of supporting rollers 15 and 16 are provided at the sides of the conveyor belts 9 and 10 facing each other.

An x-ray film cassette 8 can be optionally inserted into the x-ray loading and positioning device 6 through a loading opening 17 provided at a side of the patient support table 3, or through a loading opening 18, indicated with dashed lines in FIG. 1, provided at the side of the radiator carrier 5 which is remote from the x-ray radiator 4. Regardless of whether the x-ray film cassette 8 is loaded through opening 17 or opening 18, the x-ray film cassette 8 is first conveyed motor-driven to the stand-by position BP by means of the conveyor belts 9 and 10. When an x-ray exposure is to be made of a patient situated on the support table 3, the x-ray film cassette 8 is conveyed motor-driven to the exposure position AP, and an exposure is generated by actuation of suitable operating controls (not shown). Subsequently, the x-ray film cassette 8 is conveyed back to the stand-by position BP, or is conveyed to one of the loading openings 17 or 18, from which it can be removed.

In the examination apparatus shown in FIG. 1, the loading and positioning device is integrated with the carrier 2, such that the x-ray film cassette 8 rests on the upper side of the carrier 2, which forms the conveying plane for the x-ray film cassette 8. Since the film plane is substantially identical to the conveying plane (the film plane lying only a few millimeters above the conveying plane), the film plane has been designated with the reference symbol FE at the upper side of the carrier 2, for simplicity.

In the embodiment of FIG. 1, the radiator carrier 5 has a vertical section having a longitudinal axis which intersects the conveying path of an x-ray film cassette 8 introduced through the loading opening 18 and conveyed in the direction toward the stand-by position BP. In order to enable the conveying of a new film cassette 8 through the loading opening 18 to the stand-by position BP, the region of the radiator carrier 5 situated adjacent the film plane FE (formed by the end of the vertical section of the radiator carrier 5 adjacent the film plane FE) is forked and has legs 19 and 20 attached to the carrier 2. By providing the radiator carrier 5 with this forked construction, unimpeded passage of an x-ray film cassette 8 is achieved. An x-ray film cassette introduced through the loading opening 18 can thus be conveyed from that end of the radiator carrier 5 which is remote from the x-ray radiator 4 to the other end of the loading and positioning device 6 so as to reside at the exposure position AP beneath the x-ray radiator 4, with the x-ray film cassette 8, if necessary residing momentarily at the stand-by position BP. In other words, the x-ray film cassette 8 can be conveyed from a side of the radiator carrier 5 remote from the exposure position AP to the other side of the exposure position AP, and back, without impediment.

If the radiator carrier 5 were directly connected to the carrier 2 without the forked construction, it would be not be possible to select the conveying direction of the loading and positioning device 6 to be in the direction of the longitudinal axis of the carrier 2, and simultaneously to provide optional loading of the device 6 through the loading opening 18. In other words, it would not be possible to provide two-sided loadability of the device 6. The feature of two-sided loadability is a significant advantage, particularly in those instances wherein a sterile operation is being undertaken on a patient situated on the support table 3 under x-ray supervision. In such a situation, servicing of the loading and positioning device 6 by an attendant to the operating surgeon can ensue proceeding from the loading opening 18, so that the attendant need not move into the sterile operating area.

The components of the loading and positioning device 6 situated above the upper side of the carrier 2 are protected by a covering 22, indicated with dashed lines in FIG. 1.

In the further exemplary embodiment shown in FIG. 2, elements identical or similar to the elements described in connection with FIG. 1 are provided with the same reference symbols. In the embodiment of FIG. 2, the region of the radiator carrier 5 adjacent the film plane FE is not forked, but instead has only a single leg 22. An x-ray film cassette 8 loaded through the loading opening 18 is thus conveyed beneath the leg 22 in the conveying direction toward the stand-by position BP.

The loading and positioning device 6 can be constructed so that it can accept x-ray film cassettes of different formats, and for preparing x-ray exposures having format division.

It is also possible to arrange the loading and positioning device 6 entirely within the structure of the carrier 2.

The remote end of the radiator carrier 5 need not necessarily be attached at an extreme end of loading and positioning device 6, as shown in the embodiments of FIGS. 1 and 2, however, it must, of necessity be attached at some location along the carrier 2 which is over the conveying path within the loading and positioning device 6. The structure disclosed herein, however, permits the radiator carrier 5 to be attached at any location along the film plane FE without impeding conveying of an x-ray film cassette 8 therein. Instead of attaching the radiator carrier 5 to the carrier 2 as the bearing structure in the manner shown in FIGS. 1 and 2, the radiator carrier 5 can be attached to other bearing structure, for example to the base 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray examination apparatus comprising:

an x-ray radiator;

a radiator carrier having a first end at which said x-ray radiator is mounted and having a second end remote from said x-ray radiator;

a loading and positioning device having a manually freely accessible first loading opening for loading an x-ray film cassette into said loading and positioning device on a first side of said radiator carrier, said first side and said first loading opening being disposed on one side of and remote from said x-ray radiator, and a film plane and including means for conveying said x-ray film cassette along a conveying path entirely co-planar with said film plane from said first loading opening to an exposure position beneath said x-ray radiator and having a second manually freely accessible loading opening disposed at a second side of said x-ray radiator for optionally loading said x-ray film cassette into said loading and positioning device on said second side of said x-ray radiator;

bearing structure for bearing said loading and positioning device and said radiator carrier; and said second end of said radiator carrier having a section with a longitudinal axis, and said second end of said radiator carrier being attached to said bearing structure over said conveying path with said longitudinal axis intersecting said conveying path with no portion of said second end of said radiator carrier impeding movement of an x-ray film cassette from said loading opening to said exposure position.

2. An x-ray examination apparatus as claimed in claim 1 wherein said second end of said radiator carrier comprises two forked legs attached to said loading and position device and disposed over said film plane and straddling said loading opening.

3. An x-ray examination apparatus as claimed in claim 1 wherein said means for attaching second end of said radiation carrier comprises a single leg having a vertical position extending over said film plane and having an angled portion, disposed substantially perpendicularly to said vertical portion extending over said loading opening and attached to said loading and positioning device.

* * * * *